(12) United States Patent
Krause et al.

(10) Patent No.: US 6,981,505 B2
(45) Date of Patent: Jan. 3, 2006

(54) UROLOGICAL DEVICE FOR THE INCONTINENT MALE

(76) Inventors: William R. Krause, 820 Gilliams Mountain Rd., Charlottesville, VA (US) 22903; Dale Chadwick, 101 Inglewood Ct., Charlottesville, VA (US) 22901

(*) Notice: Subject to any disclaimer, the term of this patent is extended or adjusted under 35 U.S.C. 154(b) by 286 days.

(21) Appl. No.: 10/076,784

(22) Filed: Feb. 13, 2002

(65) Prior Publication Data

US 2002/0111640 A1 Aug. 15, 2002

Related U.S. Application Data

(60) Provisional application No. 60/268,298, filed on Feb. 13, 2001.

(51) Int. Cl.
*A61F 5/48* (2006.01)
(52) U.S. Cl. .................................... 128/885; 606/157
(58) Field of Classification Search .............. 606/1, 606/118, 135–137, 151–157, 201–204.55, 606/205–211; 24/455, 484–489, 499–511, 24/662, 19, 268–286, 459, 521; 128/885
See application file for complete search history.

(56) References Cited

U.S. PATENT DOCUMENTS

| 3,203,421 | A | * | 8/1965 | Bialick ........................ 606/157 |
| 4,821,719 | A | * | 4/1989 | Fogarty ....................... 606/158 |
| 5,571,125 | A | * | 11/1996 | Chadwick ................... 606/157 |
| 6,131,576 | A | * | 10/2000 | Davis .......................... 128/885 |

\* cited by examiner

*Primary Examiner*—Glenn K. Dawson
(74) *Attorney, Agent, or Firm*—Jagtiani + Guttag

(57) ABSTRACT

The present invention features a device to prevent the unwanted flow of urine in incontinent human males. This penile clamp is designed to provide an external pressure applied to the underside of the penis at the base thereof to close the urethral canal. The apparatus includes a rigid projection on the lower member of the device that applies a concentrated force on the canal. The upper bar of the device provides an attachment for a pad as an integral part of an easily disinfected clamp that is hinged at one end and provided with an adjustable tensioning closure device at its other end. The closure device is easily removable to allow one hand release of the penis restriction. A screw-type adjustment is easily set and is easily disassembled by a quick-release apparatus. While the clamp can be closed over the penis of an incontinent male to prevent urination, it does not appreciably restrict blood flow therein.

15 Claims, 7 Drawing Sheets

UROLOGICAL DEVICE FOR THE INCONTINENT MALE

CROSS-REFERENCE TO RELATED APPLICATIONS

This application claims benefit from U.S. Ser. No. 60/268,298 which was filed on Feb. 13, 2001 entitled Urological Clamp for Male Incontinence. The entire contents and disclosures of the above application being hereby incorporated by reference.

FIELD OF THE INVENTION

The present invention pertains to a device for restricting the flow of urine through the penis of a male and providing for the voluntary release of urine, and, more particularly, to an easily adjustable, penis-clamping apparatus for incontinent males.

BACKGROUND OF THE INVENTION

While male incontinence is a common and often neglected problem, the distress, embarrassment and inconvenience imposed on individuals suffering from involuntary urination warrants the development of non-invasive solutions to this condition.

To date, one of the common means of preventing the involuntary flow of urine in incontinent males has been to clamp the penis via a device that becomes painful, socially restrictive and difficult to keep clean. Such devices cause pressure to be applied upon the urethra, which consequently restricts the flow of urine through the penis. Another means of incontinence control is to place the penis in a pouch with a water-tight seal at the base of the penis and collect urine in a discharge bag.

U.S. Pat. No. 4,942,886 (entitled "External Incontinency Device" and issued to Timmons on Jul. 24, 1990) discloses a device having rigid members hinged together at one end and a ratchet portion with a plurality of recesses. When a strap is placed in one of the recesses, the two halves of the device are caused to maintain a predetermined position of clamping the penis. Unfortunately, due to the nature of the ratchet recess portion, inadvertent pressure against one or both of the sides of the device can cause a tightening of the device and a subsequent, excessive or pathological constriction of the penis.

One of the more popular devices for treating male incontinence is sold under the trademark Bard Cunningham Clamp.RTM. This device, too, has a ratchet-type closure mechanism that is subject to the same types of difficulties regarding any inadvertent bumping or touching thereof.

While not specifically addressing incontinence, U.S. Pat. No. 4,139,007 (entitled "Method and Apparatus for Conception" and issued to Diamond on Feb. 13, 1979) also discloses a male contraceptive device that prevents the leakage of semen into the female vagina. This device also has a ratchet recess portion, which is also subject to the same problems as experienced with Timmons.

To substitute for the rachet mechanism, Velcro® has been used in various devices. For example, U.S. Pat. Nos. 3,155,096 and 3,866,611 both feature the use of Velcro® fasteners as the closure mechanism. (The former, entitled "Male Incontinence Clamp" issued to Outwin on Nov. 3, 1964; the latter, entitled "Incontinence Device", issued to Baumrucker on Feb. 18, 1975.) Unfortunately, as lint and other foreign materials become embedded in the operating mechanism (i.e., hooks and eyes) of the material, Velcro® has a tendency to become less efficient. Over a period of time, therefore, such devices become less useful.

U.S. Pat. No. 3,203,421 (entitled "Incontinence Clamp Device" and issued to Bialick on Aug. 31, 1965) discloses a device in which a knurled knob is used to tighten together the two portions of the hinged device. The tension appears to be predetermined, and the release of the penis is accomplished by completely removing the device, thus making use thereof at a urinal impossible. Two hands are required to reposition the device. While trying to operate the device, there is also a certain risk involved in dropping any of the parts thereof.

U.S. Pat. No. 5,415,179 (entitled "Male Urinary Incontinence Device" and issued to Mendoza on May 16, 1995) discloses a device comprising a "U-shaped "lower unit with a hinged upper bar which closes across the open section of the lower unit. The upper bar has a screw mechanism with a pad that causes compression of the penis when the pad is screwed down on the penis. While this will create sufficient pressure to stop the flow of involuntary urine, there is the risk of reducing or stopping the blood flow to the penis. As there is no direct pressure on the urethra, the pressure must be applied to the entire cross-section of the penis and the pressure sufficient to close the urethra. In addition, the mechanism is not convenient for voluntary urination as the complete device must be removed and reapplied using both hands.

U.S. Pat. No. 5,571,125 (entitled "Penis—Clamping Device for the Incontinent" and issued to Chadwick on Nov. 5, 1996) discloses a hinged clamshell device that can easily open and close. The device employs a hinged section with padded rigid straight jaws that are held shut with a screw/spring closure device. The closure device allows the user to adjust the pressure applied to the penis. The closure device also employs a quick release apparatus. However the disadvantage of this device is the hinge-jaw design and the establishment of an uneven pressure distribution on the penis. Since the jaws of the device are straight and unyielding, the pressure will be greatest on the hinged side where the jaws pinch down on the penis and there is no direct pressure on the urethra.

U.S. Pat. No. 5,184,629 (entitled "Male Urinary Anti-incontinence Device and Method" and issued to Erickson and Timm on Feb. 9, 1993) discloses a hinged cradle member with an elastic strap closure mechanism. The cradle member includes integral hinges situated about an axis perpendicular to the penile shaft and interconnecting the dorsal and ventral sections of the device through which the shaft of the penis is placed. The unique aspect of this device is an integral urethral occlusion pad on the ventral member such that upon closure and securing with the elastic (velcro) strap, the urethra is occluded. The disadvantage of this device is that it folds along the length of the penis and requires a substantial length of shaft for placement. In addition, there is no means of adjusting the amount of pressure applied to the penis to occlude the urethra.

The foregoing approaches to alleviating the problem of urinary incontinence in men leave much to be desired, since these designs offer little in the way of comfort or convenience for the user. In addition, none of these clamps is easy to clean, or are any capable of adjusting pressure directly upon the urethra. It should be obvious to the casual observer that such devices are neither comfortable nor efficient in resolving the problems imposed by an incontinent condition. In fact, such clamps are sometimes not only unworkable, but are actually dangerous when residual urine burns the skin or when inadvertent tightening causes penile constriction.

There is a need for an improved penile clamp that is safe, comfortable, easily cleanable and more socially practical (i.e., utilizing one-handed operation) than that heretofore devised. The ease of attachment and usage, as well as an emergency quick release, should also be combined with infinitely variable adjustment to enable the application of different pressures to accommodate the individual needs of users. For sanitary reasons, it is preferable that the clamping device does not absorb urine through the use of absorptive materials (pads).

DETAILED DESCRIPTION OF THE PREFERRED EMBODIMENT

Figure 1:
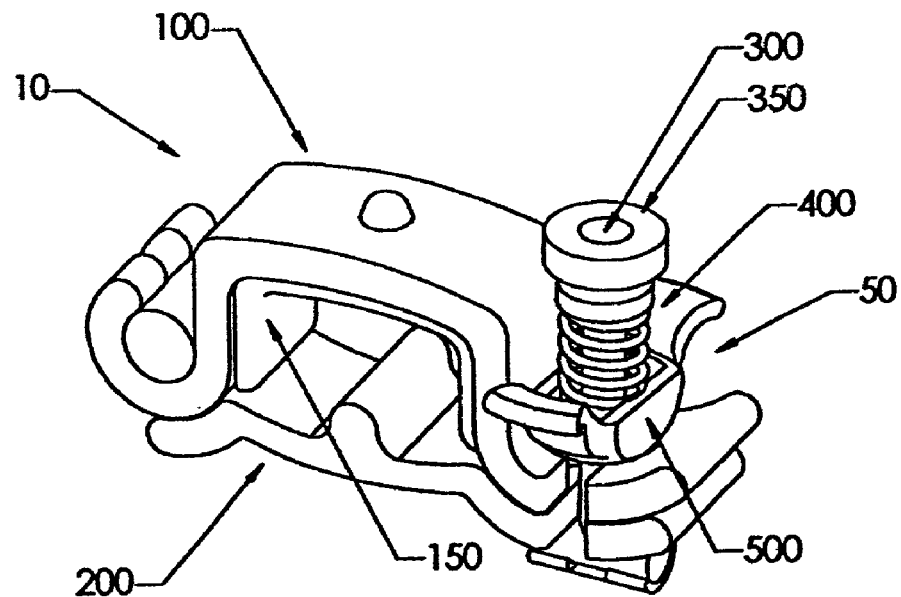
FIG. 1 is a perspective view of the clamping device of the present invention locked together in a closed position by means of the post assembly.

The present invention comprises a hinged penile clamp that is designed so that it easily opens and closes. For user comfort, the device is padded with a closed-cell non-liquid visco elastic polymer or similar padding material. The inventive clamp is designed to allow for precise pressure application by employing a screw-type, tightening adjustment for the upper and lower members. The screw-type adjustment is easily set, and is easily disassembled by means of a quick-release apparatus. Despite its being easily disassembled, the adjustment apparatus will not permanently change as a result of accidental manipulation or external forces. In addition, the device will allow for the temporary release of pressure on the urethra utilizing one-hand operation.

Although the disclosed device provides an improved method of addressing male incontinence, it also provides a method of blocking the flow of isotopes used in prostrate x-rays. The device can also be used to prevent the accidental release of urine during urological procedures when used in place of a catheter.

In male incontinence device, as illustrated in FIGS. 1–11, comprises an upper clamping bar 100 hinged about a lower body member 200 and held in place by a movable and releasable post assembly 50. The lower body member 200 has a raised portion or protrusion 215 in the approximate center of the member such that when the device is clamped about the central body of the penis 250, the protrusion 215 applies increased pressure on the urethra 255, by squeezing it between the hump and the internal structures of the penis, to prevent the flow of urine.

FIG. 1 is a perspective view of the device 10 of the present invention illustrating an upper bar 100 with an adjacent pressure pad 150 and a lower body member 200 locked together in a closed position by means of the post assembly 50. The post assembly 50 contains a post 300, a screw cap 350, a spring 400, and spring holder 500 and is described in more detail in conjunction with FIG. 10.

Figure 2:
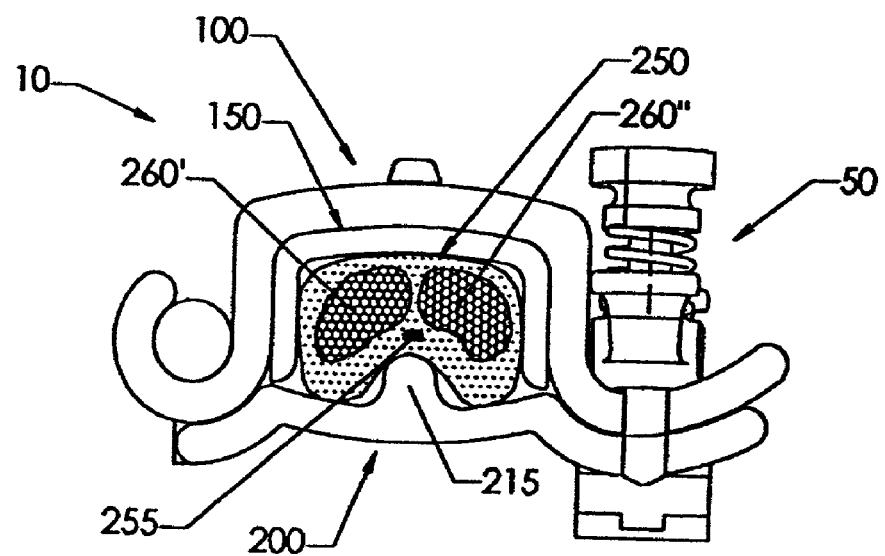
FIG. 2 illustrates the clamping action of the device with a cross sectional view of a penis.

In FIG. 2, the clamping action of the device with a cross sectional view of a penis 250 is illustrated. The clamping device 10 is positioned such that the protrusion 215 located on the lower body member 200 compresses the urethra 255 against the corpora canernosa 260', 260" within the body of the penis 250.

Figure 7:
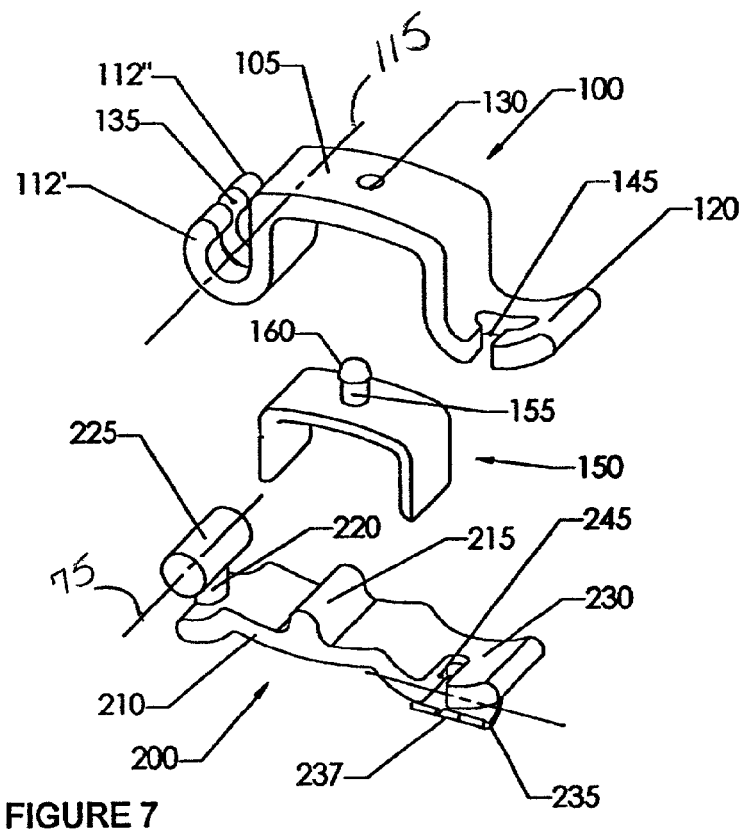
FIG. 7 is an exploded view of the components of the hinge assembly.
Figure 8:
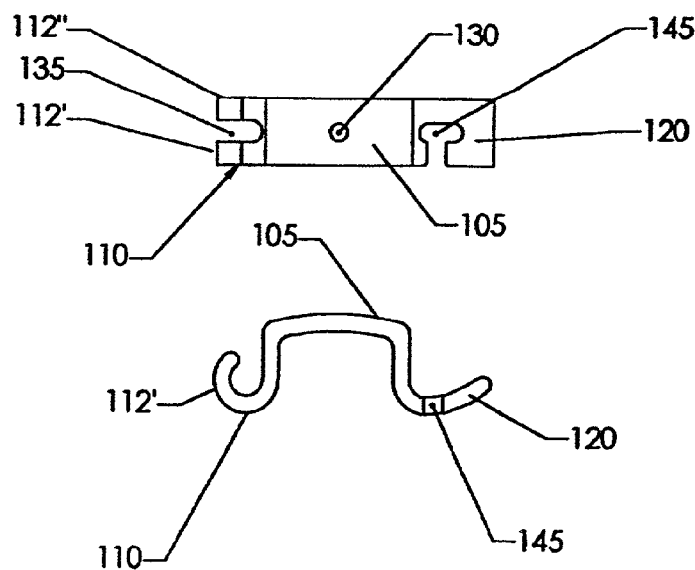
FIG. 8 is a top and side view of the upper clamping bar.
Figure 9:
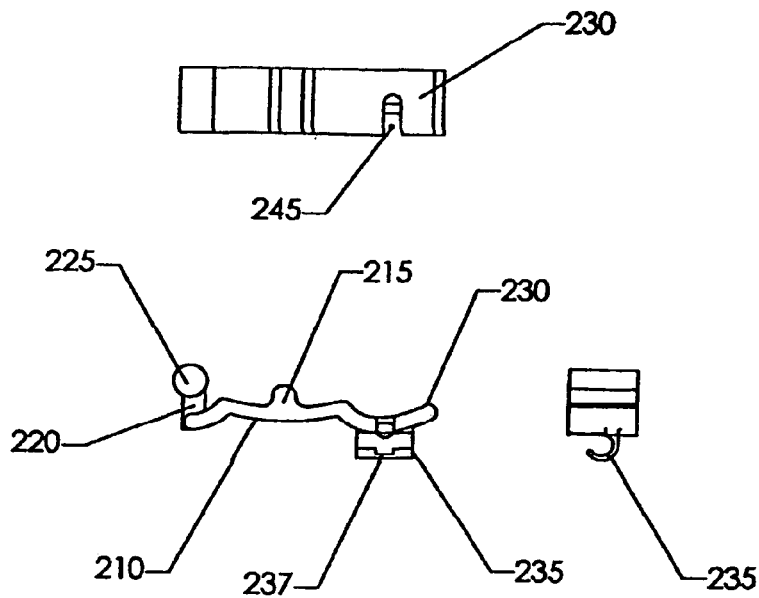
FIG. 9 is a top, side and end view of the lower body member.

As illustrated in the exploded view of FIGS. 7 and 8, the upper clamping bar 100 is preferably a "U" shaped piece having a hinge end 110, a central section 105 and a handle end 120. The hinge end 110 extends upwards and inwards forming a concentric shape about an axis 115. The hinge end 110 is comprised of two fingers 112' and 112" with a slot 135 formed between them to facilitate the connection with the lower body member 200 as illustrated in FIG. 9. The fingers 112', 112" form the hinge about the cylinder 225 of the lower body member 200. The central section 105 is generally "U" or semi-circular shaped to engage a penis. The central section 105 contains one or more holes 130, or other means, for attaching a disposable pad 150. In cross section, the central section is rectangular to provide a larger surface area for contact with the penis and decrease the risk of pressure skin necrosis. The handle end 120 extends out from the central section 105 to provide a platform for connection with the post assembly 50 and a place for the person to grasp. The slot 145 provides a receiving area for the spring loaded post assembly 50 with the upper clamping bar 100.

The disposable pad 150 is comprised of a closed cell visco-elastic polymer or similar material with a means of attachment to at least the under surface central section 105 of the upper clamping bar 100 as well as the lower bar 200 if desired. As illustrated the shape of the pad 150 is such that it will be "U" shaped or such as to be complimentary to the shape of the central section 105 of the upper clamping bar 100. The thickness of the pad will vary to accommodate different size penises and to provide the necessary counter pressure to the lower bar 200 without impeding the circulation within the penis. As illustrated, the pad 150 has molded on to the surface that contacts the upper clamping bar 100 a means of attachment with the clamping bar 100. In the illustrated embodiments, and shown in detail in FIG. 7, one or more attachment post(s) 155 and securing cap(s) 160 are positioned on the pad 150 to coincide with the attachment hole(s) 130 of the clamping bar 100. The securing cap 160 is a flexible and resilient material that will deform significantly to allow passage through the attachment hole 130 and then revert back to its original shape after passing through the bar 100 to prevent the inadvertent release of the pad 150 from the bar 100. The resilience of the material must be such, however, that it can be removed by pulling the attachment post 155 and cap 160 back through the attachment hole 130.

The lower body member 200, shown in FIG. 9, is comprised of the central section 210, the hinge post 220 and hinge cylinder 225, and the closure, or handle, end 230. The hinge post 220 and hinge cylinder 225 are positioned to provide an axis 75 about which the upper clamping bar 100 rotates. The hinge post 220 and slot 135 are dimensioned to interact with one another to enable easy rotation of the upper clamping bar 100. The central section 210 has a raised protrusion or protrusion 215 in the center of the lower body member 200 that, as stated heretofore, is dimensioned to place pressure on the urethra 255.

Figure 3:
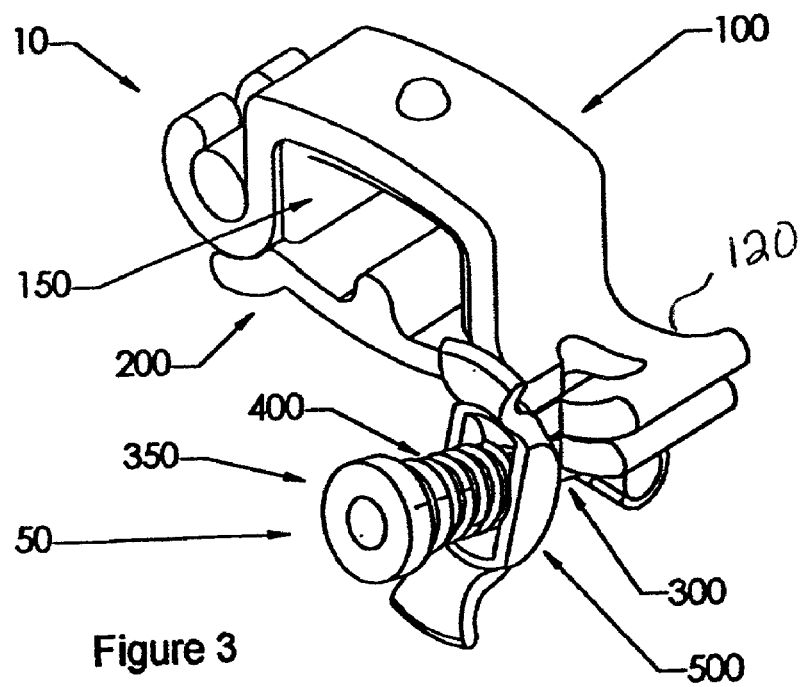
FIG. 3 is a perspective view of the clamping device in the open and unlocked position with the post assembly swung to the front.
Figure 4:
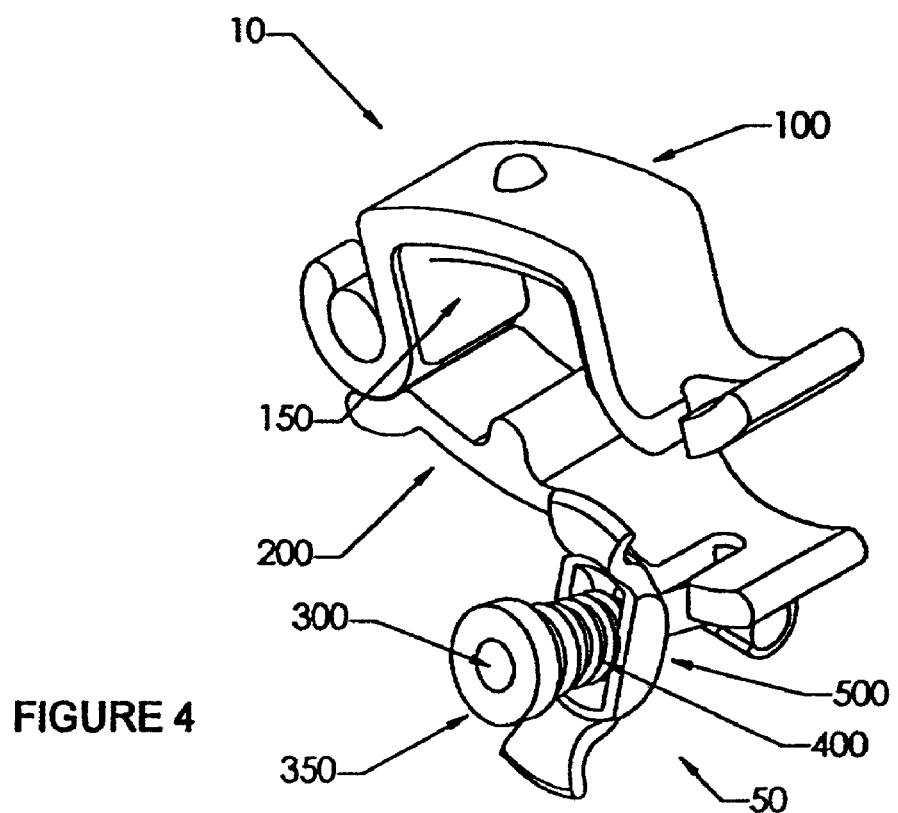
FIG. 4 is a perspective view of the clamping device in the open and unlocked position with the post assembly swung to the front and the upper clamping bar swung open.
Figure 5:
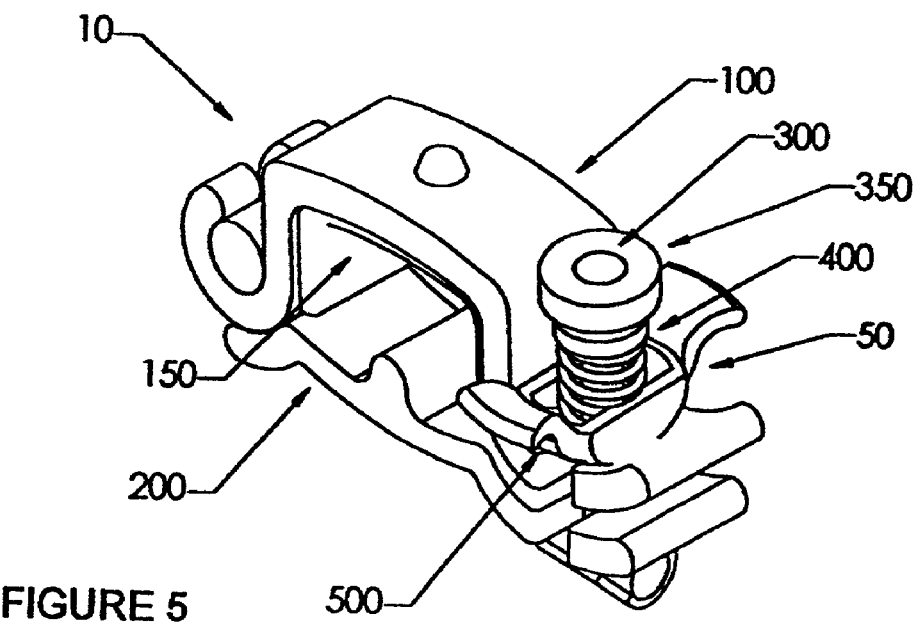
FIG. 5 is a perspective view of the clamping device in the closed position but opened slightly such that the urethra is not occluded and urine would be allowed to flow.
Figure 6:
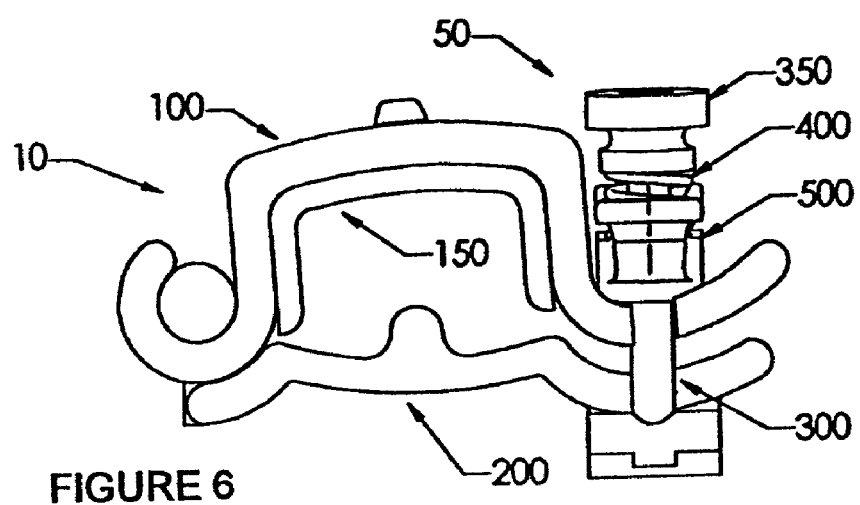
FIG. 6 is a front view of FIG. 5 showing the increased space between the lower body member and the upper bar.
Figure 10:
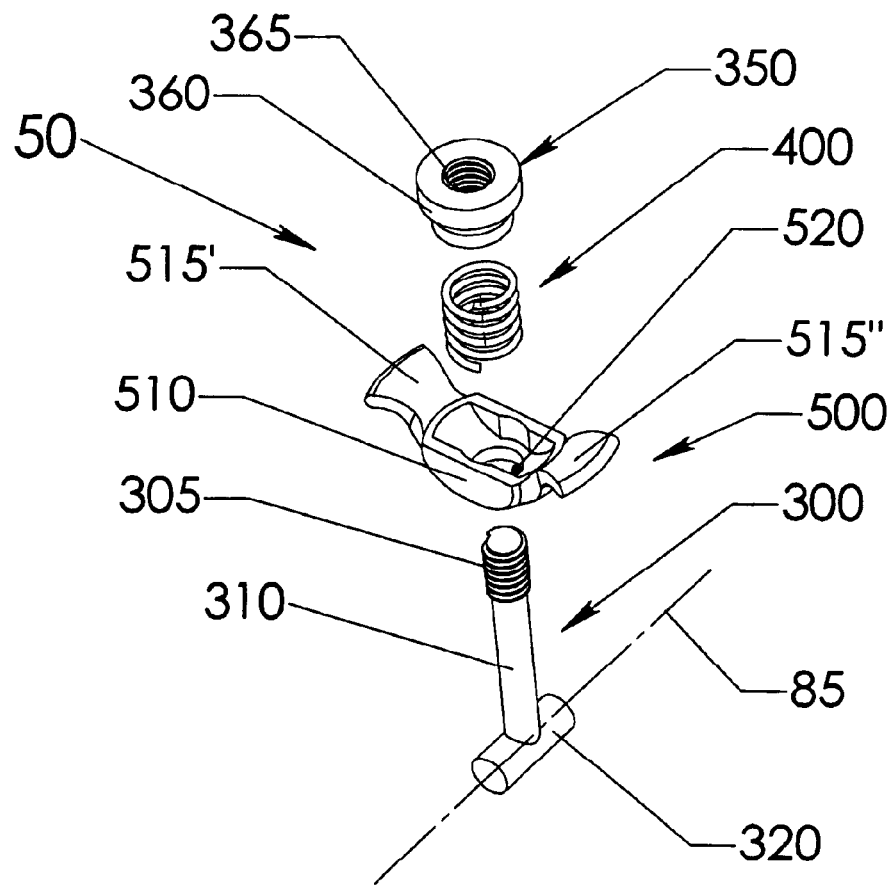
FIG. 10 is an exploded view of the components of the closure assembly.

As illustrated more clearly in FIGS. 9 and 10, the connection end 230 has a post attachment section 235 on the surface opposite to the mating surface with the upper clamping bar 100. The post attachment section 235 is designed to provide a "snap fit" of the post hinge cylinder 320 within the curved section 237 of the attachment 235. The curved section 237 has a cut out 245, as seen clearly in FIG. 9, to allow the post 310 to rotate to a plane parallel to the axis 75, as seen in FIG. 3.

Figure 11:
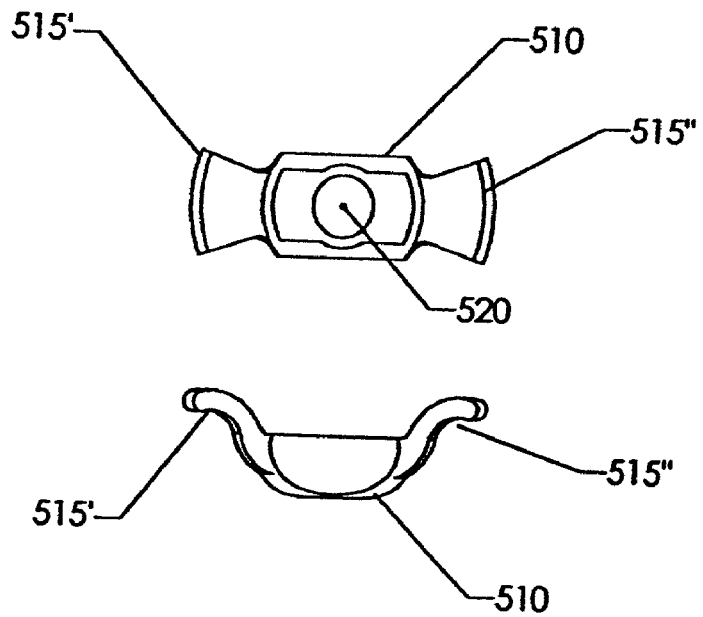
FIG. 11 is a top and side view of the spring holder.

The post assembly 50 as illustrated in FIG. 10 is comprised of post 300, an internally threaded screw cap 350, a spring 400 and a spring holder 500. The post 300 has a central body 310, preferably cylindrical, with a short post hinge cylinder 320, or other rotatable connection member, attached perpendicular to the central body 310. The post hinge has an axis 85 which, when the post hinge cylinder 320 is snapped into post attachment 235, coincides with the axis of the post attachment 235. The other end of the post 300 is a threaded section 305 for attachment of the screw cap 350. The spring 400 is a stainless steel spring with sufficient stiffness to maintain pressure against the spring holder 500, which in turn provides sufficient pressure between the upper clamping bar 100 and the lower body member 200 to prevent separation. The holder 500, as seen more clearly in FIG. 11, is of sufficient internal diameter to hold the spring 400 and has an outer spherical or partially spherical shape 510 to rest on the upper clamping bar 100. The holder 500 has two "wings" 515', 515" which provide the user with a means of grasping the holder 500 and pulling up on the holder wings 515', 515" to relieve the force exerted by the spring 400 on the upper clamping bar 100. The holder has an opening 520 dimensioned for concentric placement over the post 300. As seen in FIG. 11, the wings 515' and 515" are preferably slightly curved to provide a better, and more comfortable grip.

The preferred method of using the above-described device 10 will now be described in conjunction with FIGS. 3–5, 7 and 10. First, before the device 10 is inserted onto the penis shaft or member of a user, the closure assembly 50 is disengaged, FIG. 3 such that the upper clamping bar 100 can be rotated away from the lower body 200, FIG. 4. At this time, an area of substantial access is provided for insertion of the penis into the device 10, preferably such that the penis lies on the lower body member 200 with the protrusion 215 directly beneath the urethra 255, as illustrated in FIG. 2. The bar 100 is then rotated towards the lower bar 200 until the handle end 120 of the bar 100 is proximate the lower member 200. The closure assembly 50 is then swung upwards such that the post 310 is situated in slot 245 and slot 145 of the lower body 200 and upper bar 100, respectively, FIG. 5. In order to facilitate swinging the closure assembly 50 upwards, the spring can be compressed by grasping the spring holder 500 under the wings 515', 515" and rotating the closure assembly 50 with the holder 500 elevated above the upper bar 100. Care is taken to have in place a pad 150 that provides sufficient pressure on the penis so that the urethra 255 is occluded by the protrusion 215. The pads 150 can be supplied in various thicknesses to provide the desired compression. Additional compression adjustment can be made by compressing the spring 400 by means of the knob 350 that is threaded on to the upper portion 305 of the post 300. The knob 350 retains the spring 400 against the spring holder 500, which in turn holds the upper clamp 100 against the lower member 200. Turning the knob 350 clockwise relative to the post 300 compresses the spring 400 and applies increased pressure to the penis. In addition, increasing the compression of the spring 400 will increase the resistance of the closure assembly 50 from accidental release.

Advantageously, when the penis is located in the device 10, the clamping bar 100 confines the movement of the penis. The central section 105 of the "U-shaped" body 100 limits any side-to-side movement of the penis, thus preventing movement out from under the applied pressure. Further, because of the raised protrusion 215, increased pressure is applied directly to the urethra 255 thus decreasing the pressure required to preventing urine flow to the remainder of the penis. Further, the pad 150 provides a more comfortable engaging surface with the outer skin of the penis. This feature, along with the fact that the present arrangement does not result in any pinching or other force that constricts the blood flow through the penis, means that even when strong pressure is being applied by the protrusion 215, the device 10 can be worn for long periods of time without discomfort.

The device 10 of the present invention also has the advantage that it provides a lower uniform pressure on the outer surface of the penis at all times. Thus, opposing force, such as when the user coughs or laughs, will not result in movement of the protrusion 215 such that a reduced pressure situation occurs to allow fluid flow through the urethra 255.

When the user desires to urinate, he presses places his thumb on top of the knob 350 and a finger under each of the spring holder wings 515', 515" and compresses the spring 400. Compressing the spring 400 allows the upper clamping bar 100 to open and the pressure applied by the protrusion 215 to the urethra 255 is reduced thus allowing the urine to flow. When urination is terminated, the spring holder is released thus lowering the clamping bar and applying pressure again to the urethra 255. Thus, it can be seen that, due to the spring-loaded nature of closure 50, the device 10 can be successfully operated with one hand, without removal of the device and at no risk of losing parts of the device.

In the event of an emergency or extreme discomfort whereby the device 10 needs to be removed instantaneously, the user can simply rotate the post assembly 500 to the open position by pushing the knob 350 to the side with his thumb while grasping the lower body 200 with one or two fingers.

Figure 12:
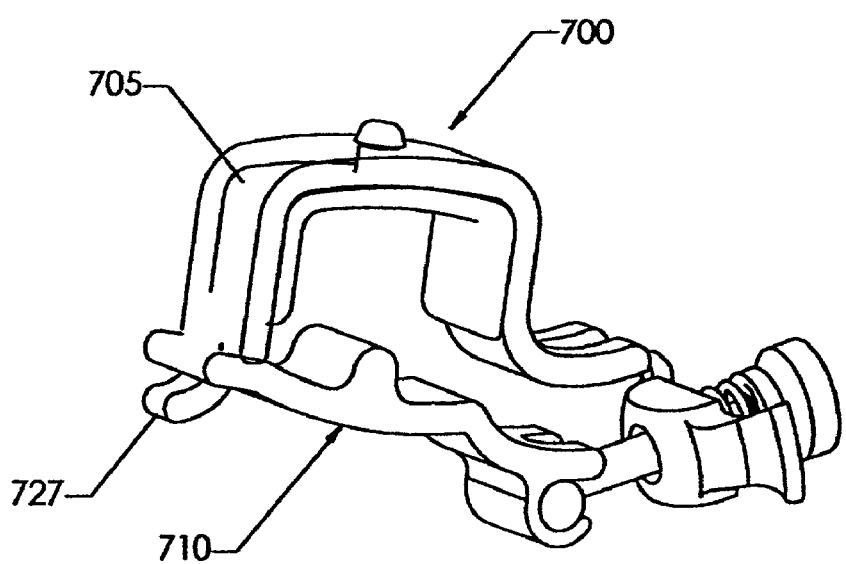
FIG. 12 is a perspective view of a the disclosed device using an alternate hinge.
Figure 13:
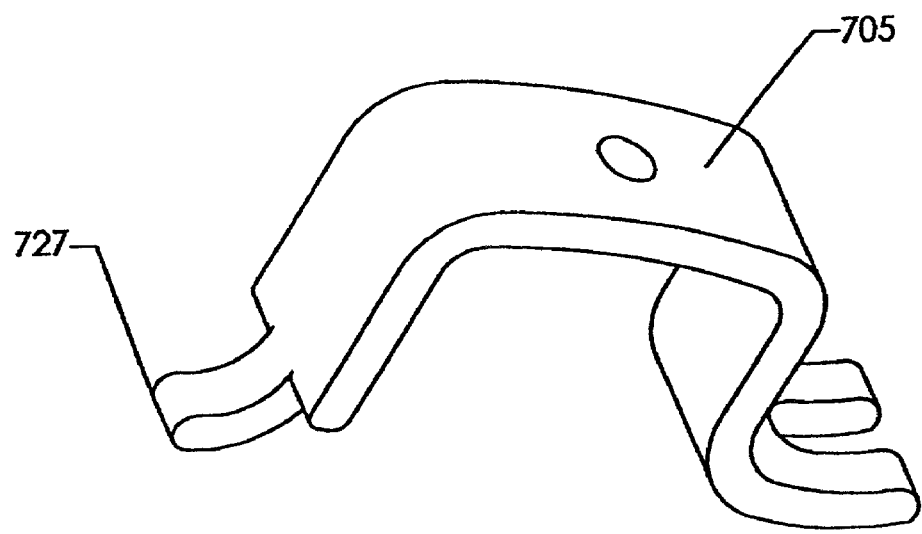
FIG. 13 is a perspective view of the top clamp of FIG. 12.
Figure 14:
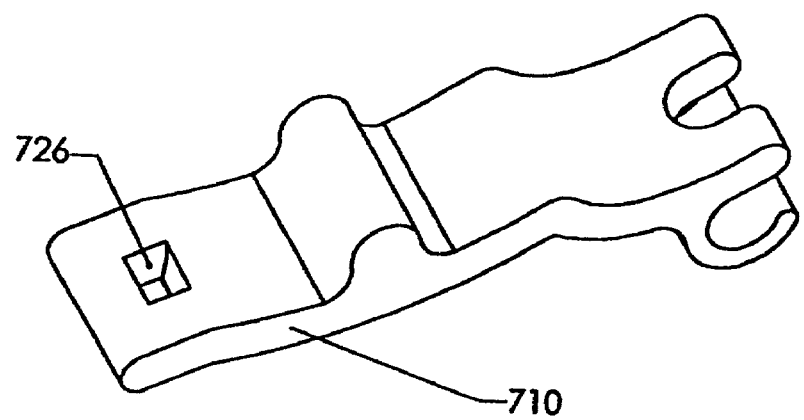
FIG. 14 is a perspective view of the bottom clamp of FIG. 12.

A further embodiment of the clamp device 700 is shown in FIGS. 12, 13 and 14 in which the hinge between the upper clamp body 705 and lower clamp body 710 has been modified. The two fingers 112 forming the hinge 110 in the embodiment of FIGS. 1–11 have been replaced with a curved extension 727 extending from the upper clamp body 705. The curved extension is dimension to fit within the slot 726 in the lower clamp body 710. The dimensioning of the slot 726, in relationship to the curved extension 727 must be such that the extension 727 can rotate freely within the slot 726 without side-to-side movement. The curvature and length of the extension 727, however, must be sufficient to prevent any separation between the upper clamp body 705 and the lower clamp body 710, thereby reducing the intended pressure and therefore effectiveness of the device 700. The remaining structure of the clamp 700 remains as described in conjunction with the foregoing embodiments. This hinge embodiment reduces the bulk and size of the device as compared to that shown in other embodiments.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Almost all of the components, especially 100, 200, 300, 350, 500, 705 and 710 can be made from a hard plastic to facilitate longevity, cleaning and ease of manufacturing. The pad 150 is preferably a closed cell, visco-elastic, resilient biocompatible polymer. The spring is preferably a non-corroding steel such as stainless steel

What is claimed is:

1. A device used to control male incontinence having:
   a.) An upper clamping bar, said upper clamping bar having an interior side and an exterior side, a first hinge end, a closure receiving end and a U-shaped central section connecting said first hinge end and said closure receiving end;
   b.) a lower rigid member, said lower rigid member having an interior side and an exterior side, a second hinge end, said second hinge end interacting with said first hinge end, a closure end, said closure end having a closure assembly attachment area, and a central section connecting said second hinge end and said closure end, said interior side of said central section having a protrusion located at approximately a center point of said interior side of said central section;
   c.) an adjustable spring biased post closure assembly, said post closure assembly being rotatably attached to said closure assembly attachment area at a distal end and having a stop at a proximal end and a spring biased gripping member between said distal end and said proximal end, said closure assembly interacting with said closure receiving end to maintain said closure receiving end proximate said closure assembly attachment area in a closed position.

2. The device of claim 1 wherein said spring biased closure assembly is adjustable to alter the distance between said closure receiving end and said closure assembly attachment area by changing the tension on a spring.

3. The device of claim 1 further comprising a removable soft compliant member dimensioned to fit within said interior of said U-shaped central section, the thickness of said compliant member adjusting the distance between said clamping bar and said lower rigid member.

4. The device of claim 3 wherein said U-shaped central section further comprises at least one affixing member, said at least one affixing member securing said soft compliant member adjacent to said interior of said U-shaped central section.

5. The device of claim 4 wherein said soft compliant member further comprises a button and said affixing member is button receiving hole to enable said soft compliant member to affixed and removed.

6. The device of claim 1 wherein said spring biased post closure assembly comprises:
   a) a T-shaped post, a distal end of said T-shaped post having a cross bar dimensioned to rotatably interact with said closure assembly attachment area and a proximal end of said T-shaped post receiving said stop, wherein said stop is a screw cap,
   b) a spring receiving area within said gripping member,
   c) a spring, said spring being dimensioned to fit within said spring receiving area and receive said T-shaped post,
   d) said screw cap being dimensioned to increase or decrease compression of said spring as said screw cap is positioned along said proximal end of said T-shaped post.

7. The device of claim 6 wherein said upper clamping bar has a upper receiving stat extending from said exterior side to said interior side at said closure receiving end and said lower rigid member has a lower receiving slot extending from said exterior side to said interior side at said closure assembly attachment area, said upper receiving slot and said lower receiving slot being dimensioned to receive said T-shaped post.

8. The device of claim 1 wherein said protrusion is shaped and positioned within said tower body member to concentrate pressure on the underside of the penis in the area of the urethra.

9. The device of claim 8 wherein said U-shaped central section further comprises at least one receiving member, said at least one receiving member securing a soft compliant member adjacent to said interior of said U-shaped central section.

10. The device of claim 1 wherein pressure is released from a user's penis for urination by pressing on said stop while holding said gripping member.

11. A device used to control mate incontinence having:
   a. an upper clamping bar, said upper clamping bar having an interior side and an exterior side, a first hinge end, a closure receiving end and a U-shaped central section connecting said hinge end and said closure receiving end, and an upper receiving slot extending from said exterior side to said interior side at said closure receiving end,
   b. a lower rigid member, said lower rigid member having an interior side and an exterior side, a second hinge end, said second hinge end rotatably interacting with said first hinge end, a closure end having a closure assembly receiving area, and a lower receiving slot extending from said exterior side to said interior side at said closure end, and a central section connecting said second hinge end and said closure end, said interior side of said central section having a protrusion located at approximately a center point of said interior side of said central section, said protrusion being shaped and positioned to concentrate pressure on the underside of the penis in the area of the urethra,
   c. a removable soft compliant member dimensioned to fit within said interior said of said U-shaped central section.
   d. an adjustable closure assembly, said closure assembly hingeably attached to said closure end of said lower body member, said closure assembly interacting with said closure receiving end to adjust said closure receiving end distance from said closure end, said adjustable assembly having:
   e. a T-shaped post, a first end of said T-shaped post having a cross bar dimensioned to rotatably interact with the closure assembly receiving area at said exterior side of said closure end and a second end of said T-shaped post being threaded to receive a screw cap, and being dimensioned to be received within said lower receiving slot and said upper receiving slot, i) a spring holder, said spring holder having a receiving hole to receive said T-shaped post, a spring receiving area and gripping members;

ii) a spring, said spring being dimensioned to fit within said spring receiving area and receive said T-shaped post iii) a screw cap, said screw cap being dimensioned to increase or decrease compression of said spring as said screw cap is positioned along said second end of said T-shaped post, wherein compression of said spring forces said closure receiving end interior side closer to said closure end interior side, thereby adjusting the distance between said U-shaped central section and said tower rigid member.

12. The method of treating male incontinence by applying pressure to the urethra comprising the steps of:
 a. rotating an adjustable spring biased post closure assembly to an open position;
 b. rotating an upper clamping bar to an open position relative to a lower rigid member;
 c. placing said lower rigid member adjacent to the underside of a penis;
 d. adjusting said lower rigid member to place a interior protrusion adjacent to the urethra of said penis;
 e. closing said upper clamping bar;
 f. compressing a gripping member to compress a spring on said closure assembly;
 g. rotating said adjustable spring biased closure assembly to a closed position;
 h. securing said spring biased closure assembly to said upper clamping bar;
 i. releasing said gripping member
 j. adjusting the clamping pressure of said adjustable closure assembly.

13. The method of claim 12 further comprising the steps of:
 a. compressing said gripping member,
 b. rotating said adjustable spring biased closure assembly about a pivot to move said adjustable spring biased closure assembly to a disengaged position from said upper clamping bar.

14. The method of claim 12 further comprising the steps of adjusting said clamping pressure of said adjustable closure member by rotating a screw cap adjacent to said spring.

15. The method of claim 12 further comprising the step of releasing said clamping pressure to permit urination without removing said device by pressing on said spring biased closure assembly while holding said gripping member.

* * * * *